United States Patent
Vestergaard Frandsen et al.

(10) Patent No.: US 8,936,801 B2
(45) Date of Patent: Jan. 20, 2015

(54) RETENTION OF PBO IN POLYMER MATRICES BY PHTHALOCYANINES

(75) Inventors: Mikkel Vestergaard Frandsen, Lausanne (CH); Sebastien Gouin, Lausanne (CH); Matthieu Zellweger, Geneva (CH); Huyen Thanh Hoang, Hanoi (VN)

(73) Assignee: Vestergaard Frandsen SA, Lausanne (CH)

( * ) Notice: Subject to any disclaimer, the term of this patent is extended or adjusted under 35 U.S.C. 154(b) by 0 days.

(21) Appl. No.: 14/115,272

(22) PCT Filed: May 2, 2011

(86) PCT No.: PCT/DK2011/050149
§ 371 (c)(1),
(2), (4) Date: Jan. 23, 2014

(87) PCT Pub. No.: WO2012/149934
PCT Pub. Date: Nov. 8, 2012

(65) Prior Publication Data
US 2014/0161856 A1   Jun. 12, 2014

(51) Int. Cl.
*A01N 25/34* (2006.01)
*A01N 25/22* (2006.01)
*A01N 25/10* (2006.01)
*A01N 53/00* (2006.01)
*A01N 37/34* (2006.01)
*A01N 43/30* (2006.01)

(52) U.S. Cl.
CPC ............... *A01N 25/22* (2013.01); *A01N 25/10* (2013.01); *A01N 25/34* (2013.01); *A01N 53/00* (2013.01); *A01N 37/34* (2013.01); *A01N 43/30* (2013.01)

USPC .......................................................... 424/409

(58) Field of Classification Search
None
See application file for complete search history.

(56) References Cited

U.S. PATENT DOCUMENTS

| 4,680,328 A | 7/1987 | Dohrer |
| 5,019,998 A | 5/1991 | Cowan |
| 5,747,057 A * | 5/1998 | Miller ........................... 424/411 |
| 6,979,455 B2 | 12/2005 | Ong |
| 2007/0196412 A1 * | 8/2007 | Karl et al. ..................... 424/411 |
| 2009/0258973 A1 * | 10/2009 | Mizukami et al. ............. 524/81 |

FOREIGN PATENT DOCUMENTS

| EP | 0582823 A1 | 7/1993 | |
| WO | 03003827 A1 | 1/2003 | |
| WO | 03063587 A1 | 8/2003 | |
| WO | 2008004711 A2 | 1/2008 | |
| WO | 2008052913 A1 | 5/2008 | |
| WO | 2008098572 A1 | 8/2008 | |
| WO | 2008128896 A2 | 10/2008 | |
| WO | 2009003468 A1 | 1/2009 | |
| WO | 2009003469 A1 | 1/2009 | |
| WO | 2009059607 A2 | 5/2009 | |
| WO | 2010016561 A2 | 2/2010 | |
| WO | WO 2010/015256 * | 2/2010 | ............. A01N 53/00 |
| WO | 2010046348 A1 | 4/2010 | |
| WO | 2010069796 A2 | 6/2010 | |

* cited by examiner

*Primary Examiner* — Brian Gulledge
(74) *Attorney, Agent, or Firm* — James Creighton Wray

(57) ABSTRACT

By incorporating PBO and phtalocyanine in a polymeric matrix, the surface concentration of the PBO after migration to the surface is reduced relatively to a matrix without phtalocyanine. This can be used to control the migration of PBO and retain PBO for a long-lasting effect.

23 Claims, 1 Drawing Sheet

Figure 1:
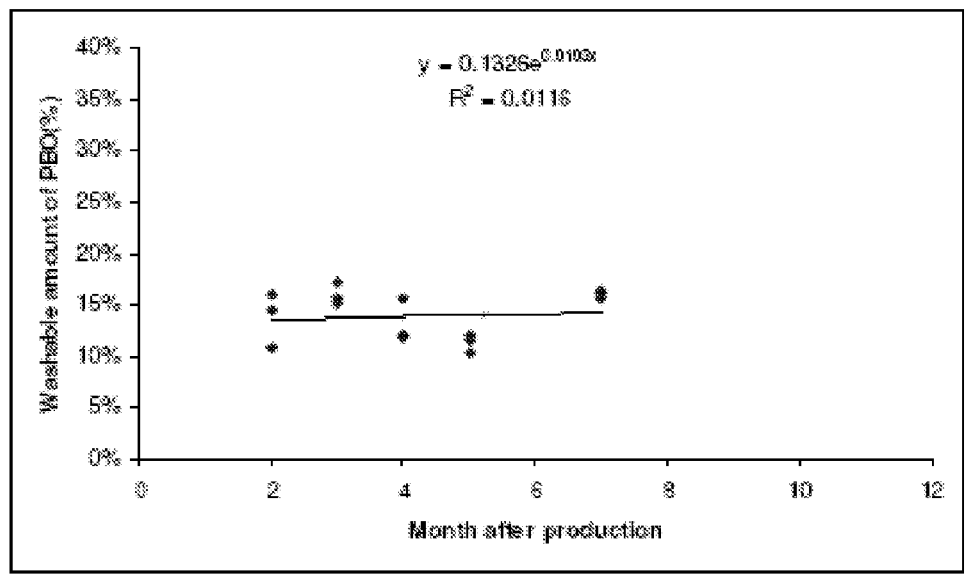

RETENTION OF PBO IN POLYMER MATRICES BY PHTHALOCYANINES

This application claims the benefit of PCT/DK2011/050149 filed May 2, 2011, International Publication No. WO 2012/149934 A1, which is hereby incorporated by reference in its entirety as if fully set forth herein.

FIELD OF THE INVENTION

The present invention relates to a method for controlling the migration of piperonyl butoxide (PBO) in a polymer matrix in which PBO is migratably incorporated and for reducing the loss of PBO from a polymer matrix. It also relates to such a matrix containing PBO.

BACKGROUND OF THE INVENTION

For insect control, it is customary to produce polymeric fibres or other polymeric articles by incorporating insecticides in the polymeric matrix of the articles and let the insecticide migrate from the bulk of the matrix to the surface of the matrix for uptake of the insecticide by insects that contact the surface. Control of migration of insecticides is of high interest, because such products, often, are intended for long term use against insects, why the migration should be fast enough for replenishing insecticide that is lost from the surface but also slow enough to guarantee a long, efficient lifetime of the article. For this reason, it is known to include migration enhancers or migration reducers in the matrix.

Adjustment of the migration is discussed in International patent application WO2008/004711 by Sumitomo concerning mainly the bleed coefficient, which is determined by a large number of factors including pigments. In the application WO2003/063587 by Vestergaard Frandsen, Carbon Black is mentioned in connection with migration of insecticides, and in Battelle's U.S. Pat. No. 5,019,998, simulation models are disclosed on Carbon Black's influence on migration. Dow's U.S. Pat. No. 4,680,328 discloses an insecticidal (chlorpyrifos) polyethylene (PE) composition for a cable with Carbon Black as compatibility additive which increases the retention time, as it is illustrated in Table II of this application when comparing sample 2 and 3, which are identical apart from a content of 2.6% carbon black (see Table I).

In the International patent application WO2008/098572 by Vestergaard Frandsen, a discussion is disclosed on migration inhibitors and migration promoters for insecticides and synergists, where it is mentioned that different substances may work differently on insecticides when compared to the effect on synergists. Some promoters or inhibitors may work more or less on deltamethrin (DM) than on piperonyl butoxide (PBO) by which the migration speed of these two components can be adjusted relatively.

The influence of different types of migration controlling agents depends on the type of agent and on the type of insecticide or synergist. Some agents are believed to take up the insecticide or synergist and act as a carrier therefore. Especially, porous particles are believed to have this property. Although Carbon Black is known as a carrier for insecticides with a retarding effect, not all porous particles necessarily are migration retarding. Interesting in this connection is the fact that kaolin, which often is regarded as a filler and carrier, for example as disclosed in WO2008/128896. Kaolin is disclosed as being migration increasing in the application WO2003/063587 by Vestergaard Frandsen. Thus, apparently, not all types of fillers that potentially can take up insecticide and synergists, like PBO, are migration retarding.

Some migration controlling agents, such as colorants, dyes, or pigments, are believed to modify the crystalline structure of the polymer, for example as discussed in Microban's U.S. Pat. No. 6,979,455. Thus, the control of migration is generally a complex process. Further, to the complexity of the retention process adds the influence of stretching, not only due to the crystallinity that changes during stretching, but also due to the formation of microvoids, as it is discussed in Sumitomo's EP582823 concerning release control.

In general, the control of the migration and retention of insecticides and synergists in polymeric matrices is of utmost concern and studies are ongoing because there is a general desire for improvements.

DESCRIPTION/SUMMARY OF THE INVENTION

It is therefore an objective of the invention to provide improvement in the art of migration control and retention control of PBO in polymeric matrices, especially, thermoplastic polymer matrices.

This objective is achieved with a polymeric matrix containing PBO and phthalocyanine e, for example metallic phthalocyanine, distributed throughout the matrix. It is also achieved with a method for controlling the migration of PBO in a polymer matrix, wherein the method comprises incorporating PBO and phthalocyanine throughout the polymer matrix.

By incorporating PBO and phthalocyanine in a polymeric matrix, the surface concentration of the PBO after migration to the surface not only is reduced relatively to a matrix without phthalocyanine but also kept stable without the typically observed increase of surface concentration with time. This effect can be used to control the migration of PBO and retain PBO in insecticidal or acaricidal products for a long-lasting effect.

As it has turned out experimentally, phthalocyanine is a very good additive for retaining PBO in a polymeric matrix, especially thermoplastic matrix. The effect of retaining PBO is not fully understood, but it occurs that phthalocyanine not only affects the migration rate of PBO. What was found experimentally was that less PBO could be washed off the surface of a matrix when the matrix contained even very small amounts of phthalocyanine. This is surprising, because it indicates that phthalocyanine affects the retention of PBO by either a smaller release of PBO from the bulk to the surface of the matrix, for example by changing the crystalline structure of the polymer, or by binding the PBO better to the surface of the matrix. The effect was a remarkably reduced wash off of PBO, which is an important factor for long-lasting insecticidal products. When washing the surface of the matrix, the apparent PBO concentration measured from the surface was only 15% of the bulk concentration and did not change with time. Thus, apparently, phthalocyanine affects the maximum achievable plateau concentration on the surface against the gradient that normally drives the PBO to the surface.

As mentioned, even small amounts of phthalocyanine, for example metallic phthalocyanine, are effective for the retention of PBO; for example the concentration of the phthalocyanine, optionally metallic phthalocyanine, is between 0.001% and 1%, or between 0.01% and 1% by weight of the matrix, or between 0.01% and 0.3% or even between 0.02% and 0.1%.

Surprisingly, the concentrations of phthalocyanine necessary for retaining PBO are much less than would be necessary to retain an insecticide such as DM. This is highly beneficial, because phthalocyanine is a good example for a retention controlling agent acting differentially between PBO and the insecticide. In other words, phthalocyanine may be used for regulating the retention of PBO without substantially affecting the migration and retention of an insecticide or acaricide, for example DM. The problem of regulating the migration and retention of insecticide and synergist in a matrix is a common problem, because it is, normally, difficult to regulate the migration and retention of one of the active components without also affecting the other. For this reason, a separation of the synergist and the insecticide/acaricide into different matrices have been proposed in International patent applications WO2009/003468 and WO2009003469 by Vestergaard Frandsen, WO2010 046348 by Intelligent Insect Control, and WO2010/016561 by Sumitomo. However, by using phthalocyanine, a differentiated release between the PBO and the insecticide/acaricide, for example DM, may be achieved even when incorporated in the same polymer matrix.

The phthalocyanine has proven effective for concentrations of PBO in the matrix, when the concentration of the phthalocyanine is between 0.001% and 1%, or between 0.01% and 1% by weight of the matrix, or between 0.01% and 0.3% or even between 0.02% and 0.1%.

Advantageous concentrations of PBO in the matrix are between 0.5% and 10% by weight of the matrix, for example between 1% and 5%.

Advantageously, the ratio between the weight concentration of PBO in the matrix relatively to the weight concentration of the phthalocyanine in the matrix is between 5 and 500, for example between 30 and 300 or between 50 and 200.

The inventions is useful for matrices of thermoplastic polymers, for example polyolefins. Polyethylene (PE) or polypropylene (PP) or a mixture thereof is a good candidate for incorporation of PBO. For example, the matrix comprises at least 75% PP or PE, or at least 90% PP or PE. Other non limiting examples are PE matrices with HDPE and containing LLDPE and/or LDPE. For example, the matrix contains at least 50% HDPE or at least 75% HDPE and, optionally, more than 5% or 10% LDPE or LLDPE.

The matrix may be used for films, for example in agricultural use but also for the production of tarpaulins. The latter are used widely for insecticidal shelters in connection with protection of humans and animals, especially in emergency situations.

Alternatively, the polymeric matrix may be a filament, for example for fabrics where monofilament or multifilament yarn is used in the production of knitted, woven or non-woven fabrics. Special attention in this respect have filaments for nets, for example bed nets, greenhouse nets, nets for crop coverage, or fences surrounding at least partly an agricultural open air area for preventing low flying insects to enter the area. The latter is explained in more detail in the International patent application WO2003003827 by Vestergaard Frandsen.

Insect nets, typically, have a mesh size of 1-5 mm, for example 1.5-2.5 mm Yarns for nets advantageously have a thickness of 75-900 denier. Useful examples for greenhouse nets are yarns with 150-600 denier. For fencing, typically, thicker yarns are used, for example 500-900 denier yarns.

Another non-limiting possible use is for covering walls as a measure against insects and/or acari; examples of wall linings are explained in International patent application WO2009/059607 by Vestergaard Frandsen, where it is also explained that a dark colour may be advantageous for wall linings with respect to mosquitoes. Such dark colour can be achieved with the phthalocyanine. As also disclosed in International patent application WO2009/059607, the product may be used for covering spaces where mosquitoes or other insects or acari can enter dwellings; for example, it can be used as a net or other kind of fabric to close the space between the upper edge of a wall in a but and the roof of the hut. The latter has great importance in Africa, where huts are constructed with such open spaces.

A further example is protection of harvested crops, for example during storage of grain. For example, in India, large parts of crops are lost during storage because of pest attack, why it is important to protect the harvested crops, for example grains in storage. For this reason, pesticidal films or textiles including sacks, bags, and nets, can successfully be used to enclose the harvested crops. In addition, pesticidal textiles can be used to surround crops, such as banana, while still connected to the plant itself.

Other non exclusive applications include curtains, window screens and door screens in livestock, horse blankets, wrapping sacks, laminated paper, construction materials, and artificial leathers.

An advantageous insecticide or acaricide concentration for products, especially such fabrics, including nets, is between 0.01% and 10%, fore example 0.1%-2%. Advantageous insecticide or acaricide concentrations are between 10 and 1000 $mg/m^2$, or between 10 and 500 $mg/m^2$ or between 20 and 250 $mg/m^2$ or between 50 and 150 $mg/m^2$ of the fabric.

The term "insect or acari" has to be read as "insect or acari or both". The term "insecticide"/"acaricide" is not meant as only one single insecticide/acaricide and does not exclude the insecticide/acaricide being part of a group of insecticides/acaricide. It should also be pointed out that many specific insecticides are also acaricides, as they act against insects as well as acari; thus, the expression "an insecticide or an acaricide" is not meant as one of them excluding the other.

For example, the matrix comprises also a pyrethroid, a pyrrole, a pyrazole, or a neonicotinoid, or a combination of these. Examples thereof are deltamethrin, chlorfenapyr, fipronil, and dinotefuran.

Other beneficial ingredients for a product according to the above include biocides, acaricides, repellents, and additives of various kinds, for example other synergists, bactericides, bacteriostatics, herbicides, UV protecting agents, preservatives, anti-hydrolysis agents, detergents, fillers, impact modifiers, anti-fogging agents, blowing agents, clarifiers, nucleating agents, coupling agents, conductivity-enhancing agents to prevent static electricity, stabilizers such as anti-oxidants, carbon and oxygen radical scavengers and peroxide decomposing agents, flame retardants, mould release agents, optical brighteners, spreading agents, antiblocking agents, anti-migrating agents, migration promoters, foam-forming agents, anti-soiling agents, antifouling agents, thickeners, wetting agents, plasticizers adhesive or anti-adhesive agents, fragrance, pigments, other dyestuffs, and oils and waxes, for example polymer oil and polymer waxes, including polyethylene waxes.

Considerations on the extrusion of fibres with a synergist and an insecticide have been published in International patent application WO2008/098572. Especially, the considerations about the design of the extrusion apparatus and about the temperature of the extruder being higher than the temperature throughout the material and the influence of the extrusion time on the insecticides and synergists can be transferred to this invention as well.

The exposure of an insect to an insecticide or an acari to an acaricide, for example deltamethrin, and PBO need not be from the same polymeric matrix. For example, the product may comprise a thermoplastic substrate with a matrix that has PBO migratably incorporated in the matrix together with phthalocyanine, and where the substrate is coated with a coating containing the insecticide/acaricide. Once, the coating is applied to the PBO-containing matrix, the PBO migrates to the surface of the matrix and from the surface of the matrix through the coating to the surface of the coating. A system of this kind is disclosed in the International patent application WO2008/098572 by Vestergaard Frandsen. For example, the substrate contains PBO and phthalocyanine but not a specific insecticide/acaricide, and the coating contains the specific insecticide/acaricide but no PBO until the PBO migrates from the bulk substrate into the coating.

A non-limiting example is a thermoplastic fibre produced by extruding a thermoplastic polymer containing PBO and phthalocyanine, and where the fibre is then coated with a formulation containing an insecticide/acaricide, for example a polymeric formulation. Such a fibre may advantageously be used for production of nets or other fabrics. Such a fibre may be a monofilament or multifilament.

In cases where the coating does not allow the PBO to migrate through the coating, or does not allow the PBO to migrate through the coating at a sufficient rate, the insecticidal coating may be applied fragmentary to the substrate, for example by spraying. As insect landing or crawling on the product would take up PBO from those locations on the matrix that are not covered by the coating and would take up the specific insecticide/acaricide from the fragmentary coating.

A different system is obtained by co-extruding a product with a first polymer matrix containing PBO and phthalocyanine but not a specific insecticide/acaricide and a second polymer matrix containing the specific insecticide/acaricide but not PBO. In this case, bulk concentrations of PBO and the specific insecticide/acaricide, respectively, and migration rates thereof can be precisely controlled. Such co-extrusion may be used to produce fibres or sheets.

A further alternative configuration is found in a fabric with a first type of yarn comprising a specific insecticide/acaricide but not PBO and with a second type of yarn comprising PBO and phthalocyanine but not the specific insecticide/acaricide. For example, these yarns are interwoven, combined in a knitting process, or the yarns are combined to a single thread before the weaving or knitting process. Furthermore, the two types of yarn may be used in combination in non-woven products. Such systems are disclosed in International patent applications WO2009/003468 and WO2009003469 by Vestergaard Frandsen, WO2010 046348 by Intelligent Insect Control, and WO2010/016561 by Sumitomo.

A further alternative is a yarn, which is co-extruded to comprise in a single yarn a first polymer with a specific insecticide/acaricide but not PBO and a second polymer with PBO and phthalocyanine but not the specific insecticide/acaricide, for example as disclosed in Wo2009/003468 by Vestergaard Frandsen, where a side-by-side configuration is disclosed with one half of the yarn being made of the first polymer and the other half by the second, or where the yarn has two quarters of the first polymer and two quarters of the second polymer. A further alternative is this respect is a yarn with a core having a polymer with the one agent and a sheath around the cores having a polymer with the other agent.

Non-limiting examples of the specific insecticide/acaricide are pyrethroids, pyrroles, pyrazoles, or neonicotinoids, or a combination of these. Examples thereof are deltamethrin, chlorfenapyr, fipronil, and dinotefuran.

Non-limiting examples of phthalocyanines are Phthalocyanine Green G (CAS 1328-53-6), Copper Polybormo-polychloro-phthalocyanine (CAS 68512-13-0), or Copper Phthalocyanine (CAS 147-14-8).

In intervals given between two values, optionally, the end points are also included.

SHORT DESCRIPTION OF THE DRAWINGS

Figure 2:
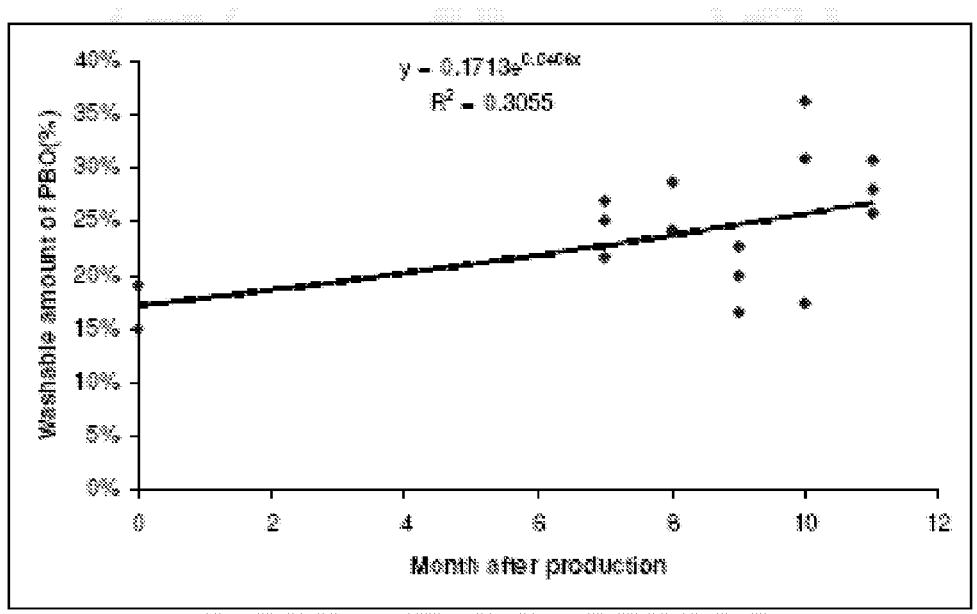

In the following, the invention is explained in more detail with reference to the drawings, wherein FIG. 1 is a graph illustrating the washable PBO amount on a PE netting including phthalocyanine in the matrix during storage in a warehouse FIG. 2 is a graph illustrating the washable PBO amount on a PE netting in the absence of phthalocyanine in the matrix during storage in a warehouse.

DETAILED DESCRIPTION/PREFERRED EMBODIMENT

Experimentally, a good product has been found in a thermoplastic polymer matrix in the form of a film or fabric containing 0.01% and 1% phthalocyanine by weight of the matrix, especially, metallic phthalocyanine; a concentration of PBO of between 10 and 500 mg/m$^2$ of the film or fabric; and containing an insecticide/acaricide. Examples of insecticides are pyrethroids, pyrroles, pyrazoles, or neonicotinoids, especially, deltamethrin, chlorfenapyr, fipronil, and dinotefuran. Concentrations of insecticides are between 0.1% and 5% of the weight of the matrix.

In the following, examples are given in connection with the invention.

EXAMPLE 1

No Phthalocyanine

A mix was prepared as per the following recipe:

| Material | % |
|---|---|
| HDPE | 72.45 |
| LDPE | 10.00 |
| Deltamethrin (10%) & Additives (10%) MB | 5.00 |
| PBO 50% MB | 5.80 |
| Additives | 6.75 |
| | 100.00 |

All master batches (MB) were based on polyethylene (PE). The percentages shown in the table are by weight relatively to the final matrix including the polymer and the active agents and other additives.

The mix was extruded into 100 denier monofilament yarns on a single-screw production extrusion line, fitted with a water-quenching tank, first stage take-up, a hot water stretching tank, a hot air annealing oven, and a 200-end-winder. Typical values (in ° C.) for the temperature ramp are set at: 180-200-210-215-215-215. The temperature in the quenching bath was 29° C., the temperature of the stretching tank was 80° C., and the temperature in the oven was 79° C. Typical draw ratios were 7-9. The yarns were then knitted into a fabric meeting the criteria set for mosquito nets by the World Health Organization's Pesticide Evaluation Scheme (WHOPES).

The development of that part of the PBO that is washable was then measured as follows. Fabric samples were stored immediately after production. The content of PBO before and after storage was followed as a function of storage time in months. It was assumed that PBO migrates to the surface progressively during storage time until equilibrium is established with the PBO content in the matrix. At that point, washable PBO reaches a plateau and does not increase with storage time any longer.

FIG. 2 illustrates typical development of washable PBO as a function of time during storage. A steady increase is observed with time within a year.

EXAMPLE 2

Containing Phthalocyanine

A mix was prepared as per the following recipe and the same drawing ratios and above conditions concerning the temperatures during production:

| Material | % |
|---|---|
| HDPE | 70.45 |
| LDPE | 10.00 |
| Deltamethrin (10%) & Additives (10%) MB | 5.00 |
| PBO 50% MB | 5.80 |
| Additives | 6.75 |
| Phthalocyanine MB (1.5%) | 2.00 |
| | 100.00 |

In this case, the washable PBO reached a plateau quickly and did not increase with storage time any longer.

The washable amount of PBO in PE netting in the absence of phthalocyanine increased from approximately 17% just after production to approximately 30% over 11 months in the warehouse, see FIG. 2.

The washable amount of PBO in PE netting containing phthalocyanine is approximately 16% constantly over 7 months, see FIG. 1.

The data suggests a plateau tendency of washable PBO both in absence and in presence of a phthalocyanine, but the plateau in nets containing a phthalocyanine is lower than in nets that do not contain phthalocyanine.

As a result, even small amounts of phthalocyanine in the polymer matrix limit the washable PBO at the surface of the matrix. As there is sufficient PBO on the surface to yield an efficient effect on insects, the limitation of PBO on the surface prolongs the lifetime of the product, as less PBO is lost during washing and handling. Whether the reason for this effect is a better retention of the PBO inside the matrix or a better retention against wash off in the uppermost surface layer is not entirely clear, however, the final effect is that the matrix is not exhausted quickly and the lifetime of the matrix with respect to PBO is increased by even minute amounts of phthalocyanine.

The invention claimed is:

1. A polymeric matrix containing piperonyl butoxide (PBO) and phthalocyanine distributed throughout the matrix, wherein the matrix is a thermoplastic polymeric extruded filament as part of a fabric, and the phthalocyanine is a metal phthalocyanine.

2. A polymeric matrix according to claim 1, wherein the concentration of the phthalocyanine is between 0.001% and 1% by weight of the matrix.

3. A polymeric matrix according to claim 2, wherein the concentration of the phthalocyanine is between 0.01% and 0.3% by weight of the matrix.

4. A polymeric matrix according to claim 1, wherein the concentration of PBO in the matrix is between 0.5% and 10% by weight.

5. A polymeric matrix according to claim 1, wherein the concentration of PBO in the matrix relatively to the concentration of the phthalocyanine in the matrix is between 5 and 500.

6. A polymeric matrix according to claim 1, wherein the polymer is a polyolefin.

7. A polymeric matrix according to claim 6, wherein the polymer comprises polyethylene (PE) or polypropylene (PP) or both.

8. A polymeric matrix according to claim 7, wherein the polymer comprises more than 50% high density polyethylene (HDPE).

9. A polymeric matrix according to claim 7, wherein the polymer comprises more than 5% low density polyethylene (LDPE) or linear low density polyethylene (LLDPE).

10. A polymeric matrix according to claim 7, wherein the polymer comprises more than 75% by weight PP.

11. A polymeric matrix according to claim 1, wherein the filament is part of a net.

12. A polymeric matrix according to claim 11, wherein the net is a bed net, a greenhouse net, a net for crop coverage, or a fence surrounding at least partly an agricultural open air area.

13. A polymeric matrix according to claim 12, wherein the net has a concentration of PBO of between 10 and 500 mg/m$^2$ of the net.

14. A polymeric matrix to claim 1, wherein the matrix has also a specific insecticide or acaricide incorporated throughout the matrix.

15. A polymeric matrix to claim 1, wherein the matrix has PBO incorporated throughout the matrix but does not contain a specific insecticide or acaricide, and wherein the matrix is coated with a coating containing the specific insecticide or acaricide.

16. A polymeric matrix according to claim 14, wherein the specific insecticide is a pyrethroid, a pyrrole, a pyrazole, or a neonicotinoid, or a combination of these.

17. A polymeric matrix according to claim 16, wherein the specific insecticide is deltamethrin, chlorfenapyr, fipronil, or dinotefuran, or a combination of these.

18. A method for controlling the migration of piperonyl butoxide (PBO) in a polymer matrix, wherein the method comprises incorporating PBO and phthalocyanine throughout the polymer matrix, wherein the matrix is a thermoplastic extruded filament as part of a fabric, and the phthalocyanine is a metal phthalocyanine.

19. A method according to claim 18, wherein the phthalocyanine concentration is between 0.001% and 1% by weight of the matrix.

20. A method according to claim 18, wherein the metal phthalocyanine is at a concentration of between 0.01% and 0.3% by weight of the matrix.

21. A method according to claim 18, wherein the concentration of PBO in the matrix is between 0.5% and 10% by weight of the matrix.

22. A method according to claim 18, wherein the concentration of PBO in the matrix relatively to the concentration of the phthalocyanine in the matrix is 5 to 500.

23. A method according to claim 18, wherein the method comprises providing the matrix as a filament in a net or other type of fabric or providing the matrix as a film, and using the net, fabric or film as a protective enclosure for harvested grains in storage.

* * * * *